(12) United States Patent
Johnson et al.

(10) Patent No.: US 12,226,571 B2
(45) Date of Patent: Feb. 18, 2025

(54) APPARATUS AND METHOD FOR EARLY DETECTION OF VENTILATOR ASSOCIATED PNEUMONIA

(71) Applicant: BOARD OF REGENTS, THE UNIVERSITY OF TEXAS SYSTEM, Austin, TX (US)

(72) Inventors: Benjamin G. Johnson, Buda, TX (US); Michelle Colleen Cole, Anchorage, AK (US); Chase Christenson, San Antonio, TX (US); Mikayla Li Rahman, Colorado Springs, CO (US); Teja Guda, San Antonio, TX (US)

( * ) Notice: Subject to any disclaimer, the term of this patent is extended or adjusted under 35 U.S.C. 154(b) by 859 days.

(21) Appl. No.: 17/234,544

(22) Filed: Apr. 19, 2021

(65) Prior Publication Data

US 2021/0330905 A1    Oct. 28, 2021

Related U.S. Application Data

(60) Provisional application No. 63/011,830, filed on Apr. 17, 2020.

(51) Int. Cl.
*A61M 16/00* (2006.01)
*A61M 16/04* (2006.01)

(52) U.S. Cl.
CPC .... *A61M 16/0003* (2014.02); *A61M 16/0402* (2014.02); *A61M 2205/3317* (2013.01)

(58) Field of Classification Search
CPC ... A61M 16/04; A61M 16/0402; A61B 5/053; A61B 5/08; A61B 5/14507; A61B 5/0538
See application file for complete search history.

(56) References Cited

U.S. PATENT DOCUMENTS

| | | | | |
|---|---|---|---|---|
| 5,024,228 | A  * | 6/1991 | Goldstone | A61B 5/6853 600/380 |
| 2004/0210114 | A1 * | 10/2004 | Simon | A61M 16/0484 600/185 |
| 2009/0281443 | A1 * | 11/2009 | Hengstenberg | A61B 5/082 600/532 |
| 2010/0022950 | A1 * | 1/2010 | Anderson | A61B 1/00114 604/100.01 |
| 2011/0071379 | A1 * | 3/2011 | Rea | A61B 5/6853 29/887 |
| 2011/0144469 | A1 * | 6/2011 | Connolly | A61B 5/1468 600/377 |
| 2013/0041238 | A1 * | 2/2013 | Joseph | A61L 29/041 600/323 |
| 2019/0060556 | A1 * | 2/2019 | Huiszoon | A61M 5/001 |
| 2020/0254216 | A1 * | 8/2020 | Varun | A61M 25/0069 |

* cited by examiner

*Primary Examiner* — Margaret M Luarca
(74) *Attorney, Agent, or Firm* — Nevrivy Patent Law Group P.L.L.C.

(57) ABSTRACT

The present invention provides an apparatus for detection of ventilator associated pneumonia (VAP) in a patient, the apparatus comprising: an endotracheal tube; at least two non-selective electrode contacts located in proximity to each other within the endotracheal tube, the contacts lacking any structural feature or component that particularly recognizes a chemical or biological species; an electrical subsystem that is capable of generating, receiving and processing electrical signals; wiring for connecting each of the electrode contacts with the electrical subsystem; and tubing for insulating the wiring from any sputum material that is introduced into the endotracheal tube by the patient.

16 Claims, 14 Drawing Sheets

Fig. 8

```
/*
 *Sends waveform to DAC0 channel.
 *Sin waves only
 */ include "Waveforms.h"

volatile int wave0 = 0;

int i = 0;
int sample = 0; //Frequency variable
int v = 0;

void setup() {
  analogWriteResolution(12);  // set the analog output resolution to 12 bit (4096 levels)
  analogReadResolution(12);   // set the analog input resolution to 12 bit Serial.begin(9600);
  pinMode(A0, INPUT); //Reference input with known resistance
  pinMode(A1, INPUT); //Testing input with unknown resistance, probe connectes here
} void loop() { analogWrite(DAC0, waveformsTable[0][i]);   // write the waveform on DAC0 i++; //increment through waveform table if(i == maxSamplesNum){  // Reset the counter to repeat the wave
    i = 0;
    sample = sample + 5; //Updates frequency from min to max, 0 to 4096Bit
    if(sample > 4095)
      sample = 0;
  }
  v = (analogRead(A0)-analogRead(A1));
  Serial.println(v);

delayMicroseconds(sample);   // Hold for sample time depending on frequency
}
```

Fig. 9

| Component | Function | Potential Failure Mode | Potential Failure Effects | S e v | Potential Cause of Failure | O c c | Current Process Controls | D e t | RPN (S*O*D) | Action Taken | Corrective Action | | | RPN (S*O*D) | Percent Change in RPN |
|---|---|---|---|---|---|---|---|---|---|---|---|---|---|---|---|
| | | | | | | | | | | | SEV | OCC | DET | | |
| Endo-tracheal Tube | Serve as a standard ETT | Mechanical Properties Altered | Airflow is altered or blocked | 8 | Misplacement of the tube | 8 | Qualified Surgeon | 7 | 448 | N/A | 8 | 8 | 7 | 448 | 0.00% |
| | | | | | Chemical Degredation | 3 | Material Selection | 3 | 72 | N/A | 8 | 3 | 3 | 72 | 0.00% |
| | | | | | Change in body position | 4 | Trained Hospital Staff | 5 | 160 | N/A | 8 | 4 | 5 | 160 | 0.00% |
| | Hold components in place | Components dislodged | Signal Lost | 6 | PVC Rupture | 2 | Material Selection | 5 | 60 | N/A | 6 | 2 | 5 | 60 | 0.00% |
| Signal Generator | Provide signal with set voltage and range of frequencies to the electrodes | Output signal different from expected | Spectrums over time are created using different signals (gives incorrect results) | 7 | Fluctuations in signal intensity (V) | 3 | Signal Generator Amplitude Control System | 7 | 147 | Calibration test cycle | 7 | 3 | 4 | 84 | 42.86% |
| | | | | | Frequency Sweep faster or slower than expected | 2 | Signal Generator Frequency Control System | 7 | 98 | Calibration test cycle | 7 | 2 | 4 | 56 | 42.86% |
| Coaxial Cables | Connect the electrode to the signal generator | Connection between components is lost | Signal Lost | 6 | Excessive ETT movement | 4 | Trained Hospital Staff | 3 | 72 | N/A | 6 | 4 | 3 | 72 | 0.00% |
| | | | | | Poor signal generator connection | 5 | N/A | 2 | 60 | Calibration test cycle | 6 | 5 | 1 | 30 | 50.00% |
| | | | | | Poor electrode connection | 5 | N/A | 2 | 60 | Calibration test cycle | 6 | 5 | 1 | 30 | 50.00% |

Fig. 9 (Cont.)

| | | | | | | | | | | |
|---|---|---|---|---|---|---|---|---|---|---|
| Voltmeter | Calculate voltage of incoming signal and output to single board computer | Voltage detected is different from actual | Erroneous Data Output | 7 | Voltmeter not calibrated properly | 2 | N/A | 7 | Function generator signal is split between electrodes and directly to voltmeter to serve as a control | 7 | 3 | | 85.71% |
| | | | | | | | | 98 | | | | 14 | |
| | Alert medical staff of detected concentrations of bacteria | Medical Staff do not recieve alert notification | Medical staff is not notified | 5 | Alert system failure | 2 | N/A | 3 | Calibration test cycle | 5 | 3 | 30 | 66.67% |
| | | | | | Connection from device to alert system is lost | 3 | N/A | 3 | Calibration test cycle | 5 | 3 | 45 | 66.67% |
| | | Not distinguishable between other normal hospital noises/alerts | Medical staff is unaware of alert | 4 | Alert is not responded to by medical staff | 5 | Trained Hospital staff to know when to respond | 3 | New alert system (examples: louder) | 4 | 3 | 60 | 40.00% |
| Alert System | Analyze incoming data from voltmeter | VAP incorrectly identified | Erroneous Data Output | 7 | Unexpected spectrum values | 6 | N/A | 5 | Index additional strains | 7 | 3 | 210 | 60.00% |
| | | | | | Over-sensitivity | 6 | N/A | 5 | Appropriate percent change determined w/ product testing | 7 | 3 | 210 | 50.00% |

APPARATUS AND METHOD FOR EARLY DETECTION OF VENTILATOR ASSOCIATED PNEUMONIA

FIELD OF THE INVENTION

The field of this invention relates to an apparatus and method for detection of ventilator associated pneumonia.

BACKGROUND OF THE INVENTION

Ventilator Associated Pneumonia (VAP) is a pneumonia that develops in a patient dependent on a ventilator 48-72 hours after undergoing mechanical ventilation by endotracheal tube (ETT) or tracheostomy. A patient intubated with a ventilator is more easily infected with bacteria than are other hospital patients because the ETT holds the throat open and mucus stagnates around the end of the tube, providing an environment where bacteria can thrive. Some tube positions are better than others, and VAP can be correlated to ETT placement. Clinically, VAP is defined as any pneumonia contracted more than 48 hours post-intubation. See, e.g., *Report on the Burden of Endemic Health Care-Associated Infection Worldwide; Clean Care is Safer Care*, World Health Organization 2011, Geneva.

Although the exact mechanism of infection is likely multivariable and is not yet fully defined, the probable pathogenesis stems from contaminated oropharyngeal secretions pooling over the ETT cuff and subsequently draining down to the lungs through a hydrostatic gradient made possible by the ETT acting as a bypass of normal physical barriers for pathogen entry (i.e., the larynx, cilia, and gravitational gradient). Mietto, C., et al., *Ventilator associated pneumonia: evolving definitions and preventive strategies*, Respiratory Care 2013, 58(6): 990. This often results in biofilm formation, giving the invading pathogens a protected reservoir to elude antibiotic therapy. Fernandez-Barat, L., et al., *Biofilms in ventilator-associated pneumonia*, Future Microbiology 2016, 11(12): 1599-1610.

According to the World Health Organization, 30% of all intensive care unit (ICU) patients in high-income countries will contract at least one healthcare-associated infection. World Health Organization 2011, supra. VAP is the most common healthcare-associated infection among US intensive care unit life support patients. Reed, D., et al., *Infection control and prevention: a review of hospital-acquired infections and the economic implications*, Ochsner Journal 2009, 9(1): 27-31. Of all ICU patients, 54% are at risk for contracting healthcare-associated pneumonia. Ibn Saied, W., et al., *A Comparison of the Mortality Risk Associated With Ventilator-Acquired Bacterial Pneumonia and Nonventilator ICU-Acquired Bacterial Pneumonia*, Critical Care Medicine 2019, 47(3): 345-352. An estimated 300,000 contract VAP in the United States annually. VAP is associated with a 38% increase in 30-day mortality and has an overall mortality rate of 28.4%. Id. Viral infections such as the recent pandemic of the novel coronavirus SARS-Cov-2 (CoViD-19) increase the body's susceptibility to infection such as VAP Immunologically compromised patients are also placed at increased risk for infection and death. Outside of the pandemic, pneumonia is the most common infection seen in the ICU, causing about 30,000 deaths per year.

VAP is the second most common nosocomial (hospital-acquired) infection, affecting 27% of all critically ill patients, and has an estimated national cost of $27 billion. Of all pneumonia cases, 86% are associated with mechanical ventilation. There were 790,257 hospitalizations involving mechanical ventilation in 2005, representing 2.7 episodes of mechanical ventilation per 1000 population. Estimated national costs were 27 billion, representing 12% of all hospital costs. There are between 250,000 and 300,000 cases of VAP per year, with an incidence rate of 5 to 10 cases per 1,000 hospital admissions.

The most common healthcare-associated infections cost the United States nearly 10 billion dollars annually. VAP accounts for a 31.6% share of that figure, with an average per-patient cost of $40,144. In another study in the Shock Trauma Intensive Care Unit, it was found that VAP not only leads to a significant increase in ventilator days and ICU length of stay, but adds substantially to hospital costs. In the ICU, an episode of VAP can cost about $57,000 per occurrence, for example. Cocanour, C. S., et al., *Cost of a ventilator-associated pneumonia in a shock trauma intensive care unit*, Surg. Infect. (Larchmt) 2005, 6(1): 65-72.

Half of all antibiotics prescribed in the ICU are for VAP, yet it is still deadly, with mortality rates as high as 76%. Vincent, J. L., et al., *The prevalence of nosocomial infection in intensive care units in Europe: Results of the European Prevalence of Infection in Intensive Care (EPIC) Study. EPIC International Advisory Committee*. J. Amer. Med. Assoc. 1995, 274(8): 639-44; Charles, M. P., et al., *Ventilator-associated pneumonia*. Australas. Med. J. 2014, 7(8): 334-44. VAP is correlated with an average 9-day extension in length of stay (LOS) in the ICU resulting in an average >$40,000 increase in cost per patient. Reed, et al., supra; Cocanour, C. S., et al., supra. The opportunity for improvement is striking. All healthcare-associated infections are preventable, but up to 30% of ventilator associated pneumonias are treated inadequately. Inweregbu, K., et al., *Nosocomial infections*, Continuing Education in Anaesthesia Critical Care & Pain 2005, 5(1): 14-17. In just the top three U.S. hospital systems, 900,000 ICU patients annually are at risk for VAP. Timely detection of the infection could reduce LOS in the ICU by six days, saving $24K per VAP patient, or $3600 per ICU patient.

Due to the baby boomer population increasing in age, there is an increasing need for ventilator use in hospitals. According to the U.S. Census Bureau, 78.0 million people in 2030 and 98.2 million people in 2060 are expected to be 65 years or older, so the incidence of VAP may be expected to grow.

Known methods for early detection of VAP are limited. Brown, et al., US 2009/0155770 A1, discloses implantable devices for fiber optic based detection of nosocomial infections. This method carries the disadvantage that a separate detection mode must be worked out for each pathogen. Some pathogens naturally fluoresce, and others may require addition of a dye for visualization. Also, the optical clarity of the sputum is not necessarily constant. The apparatus would require a light source, optical fiber, an optical detector and associated connections.

Several patent applications have addressed this problem using "electronic nose" technology. See, e.g., Burch, et al., U.S. Pat. No. 7,819,803 B2; Kea-Tiong, et al., U.S. Pat. No. 9,125,590; Weda, et al., US 2019/0167152 A1. The method makes use of a sensor array to specifically detect a "marker gas," a gas that can serve as an indicator of certain microorganisms or a pattern of odors (sensor responses) associated with a particular infection. With regard to VAP, the method involves analysis of exhaled breath from a patient on a ventilator. As with the optical method, the electronic nose methods require some complexity in the construction of the necessary apparatus.

Kuzelka, US 2019/0274633 A1 discloses a system for detecting VAP that is based on detection of volatile organic compounds (VOCs) in the exhaled breath of the patient. However, this information alone does not provide detailed bacterial species information about an infection.

Although VAP is one of the most common hospital diagnoses, there is no standard diagnostic tool that can identify the presence of VAP in real-time, in vivo and at an early stage. Physicians have only limited preventative measures for containing the burden of VAP on the healthcare system including: 30 degrees head elevation, cuff pressure monitoring, avoidance of sedatives and muscle relaxants, etc. Choudhuri, A. H., *Ventilator-Associated Pneumonia: When to hold the breath?*, International Journal of Critical Illness and Injury Science 2013, 3(3): 169-174. The current standard of detection is a daily complete blood count (CBC) for leukocytosis or increased white blood cell count. These are only general indicators of infection and may take up to 24 hours to process, translating to a total possible delay of 24 to 48 hours between infection onset and medical intervention. Also, the CBC does not indicate the source of infection. There remains a need in the art for improvement in the area of early detection of VAP with a passively operated high-fidelity device that allows for increased monitoring frequency and accurate and efficient identification of the presence of VAP in real time. The need is for an apparatus that is simple and provides information continuously and noninvasively, with as much particularity as possible, about the infection.

This background information is provided for informational purposes only. No admission is necessarily intended, nor should it be construed, that any of the preceding information constitutes prior art against the present invention.

SUMMARY OF THE INVENTION

It is to be understood that both the present general description of the embodiments and the following detailed description are exemplary, and thus do not restrict the scope of the embodiments.

The present invention meets the above described need, requiring the addition of only two electrode contacts and the associated insulated connecting wires to an inside surface of an endotracheal tube of a ventilator. Selective electrode sensors are not needed when pathogens are identified using Electrochemical Impedance Spectroscopy (EIS). EIS is the measurement of the electrochemical impedance across an electrode-electrolyte interface that is measured over a range of frequencies to elicit information about the substance of the interface. This method allows for detection of materials and organisms to be measured at this interface without the need of surface recognition elements. This mechanism has been shown to measure concentrations of *Staphylococcus aureus* as well as other bacteria including *Escherichia coli, Pseudomonas aeruginosa, Pseudomonas stutzeri* and *Staphylococcus epidermidis*. A. C. Ward, et al., *Identification and characterization of Staphylococcus aureus on low cost screen printed carbon electrodes using impedance spectroscopy*, Biosensors and Bioelectronics 2018, 110: 65-70. However, no clinical application of this technology has been developed to assess these bacterial strains in human mucus. The present invention will be the first to deliver results affecting patient care. The present invention will accomplish this by determining the presence and concentration of *Staphylococcus aureus* specifically and could be applied to other bacterial strains.

Practitioners in this field will appreciate that the present invention will detect pathogens within a patient's mucus directly, not via evolved gases or metabolic byproducts. In some embodiments, there is no complexity in the interface of the inventive apparatus with mucus, no nanostamped or shape-selective sensors, no light source or phototube and no need for a special sampling step. The electrical signals can be analyzed to determine the presence and concentrations of various bacteria that are commonly encountered in VAP. These measurements are taken by electrodes inside the endotracheal tube and are sent to an alert system that will notify medical staff if bacteria are detected.

In certain aspects, the present invention can take the form of an apparatus for early detection of Ventilator Associated Pneumonia (VAP) in a patient. In some embodiments, the patient is dependent upon a ventilator. In some embodiments, the apparatus comprises an endotracheal tube; at least two non-selective electrode contacts located in proximity to each other within the endotracheal tube, the contacts lacking any structural feature or component that particularly recognizes a chemical or biological species; an electrical subsystem that is capable of generating, receiving and processing electrical signals; wiring for connecting each of the electrode contacts with the electrical subsystem; and tubing for insulating the wiring from any sputum material that is introduced into the endotracheal tube by the patient.

In certain embodiments of the inventive apparatus, the electrical subsystem can generate at least two distinct and oscillating electrical signals, the distinct electrical signals having distinct frequencies, each electrical signal being associated with an oscillating current that passes through the sputum material, enabling the electrical subsystem to calculate an impedance associated with each electrical signal, the plurality of impedances constituting a pattern of impedances.

In embodiments of the present invention, the pattern of impedances can correlate with a particular species of bacteria.

In embodiments of the present invention, the identified species of bacteria can include *Pseudomonas* spp. including *P. aeruginosa, Streptococcus* spp. including *S. pneumoniae* and *S. aureus, Hemophilus* spp. including *Hemophilus influenza, Escherichia coli, Klebsiella* spp. including *Klebsiella pneumonia, Enterobacter* spp., *Proteus* spp., *Serratia* spp. including *Serratia marcescens, Acinetobacter* spp., *Citrobacter* spp., *Neisseria* spp., *Stenotrophomonas maltophilia, Corynebacterium* spp., *Moraxella* spp. and/or *Enterococcus* spp.

Embodiments of the present invention can include a method for detecting Ventilator Associated Pneumonia (VAP) in a patient using the above-described apparatus. In some embodiments, the patient is intubated on a ventilator, and the apparatus can be placed inside of the endotracheal tube of the ventilator. In some embodiments, the endotracheal tube of the apparatus replaces the endotracheal tube of the ventilator and can be connected to a ventilator itself, for example, using an adaptor to connect the endotracheal tube to the ventilator.

In certain embodiments, the above-described apparatus can further comprise a computer that assists the electrical subsystem with signal processing and identification of one or more bacterial species that is/are present in the sputum material.

In some embodiments, the pattern of impedances can correlate with the presence of a plurality of species of bacteria, and the method can further comprise a determination of relative concentrations of the species of bacteria.

In embodiments of the invention, the electrical contacts are gold plated.

In other embodiments of the invention, the electrical contact surfaces can be carbon, platinum, or nickel.

In certain embodiments, the insulating tubing can be silicone tubing.

In some embodiments, the insulating tubing can be fixed to an inside surface of the endotracheal tube with a biocompatible adhesive.

In other embodiments, the insulating tubing can be continuous with an inside surface of the endotracheal tube.

In some embodiments, the wiring can comprise a chromium/nickel/molybdenum alloy.

In some embodiments, the endotracheal tube can have an internal diameter of about 7.5 mm.

In some embodiments, each electrode contact can be separated by a gap of about 0.8 mm from another electrode contact.

In some embodiments, sputum material can fill the gap.

In another aspect, the invention can include a method for detecting Ventilator Associated Pneumonia (VAP) in a patient who is intubated with an endotracheal tube and dependent upon a ventilator, the method comprising fitting an inside surface of the endotracheal tube prior to the intubation with at least two electrode contacts in proximity to each other and insulated conductive wiring connecting the electrode contacts with an electrical subsystem that is capable of generating, receiving and processing electrical signals; directing the electrical subsystem to sequentially provide at least two alternating current signals to the electrode contacts, thereby allowing the electrical subsystem to derive an impedance corresponding to each alternating current signal, the multiple derived impedances forming a pattern of impedances; and matching the pattern of impedances to a pattern of impedances known to be associated with a particular bacterial pathogen or a particular combination of bacterial pathogens.

In some embodiments, the method of the invention can further comprise using the impedance data to determine a concentration of the particular bacterial pathogen or to determine a concentration for each pathogen in the combination of bacterial pathogens.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 8 shows the Arduino code for generating the sinusoidal waveform and supplying same to electrical probe and through a reference pathway and comparing the two values to determine profile of material at the end of the probe.

FIG. 9 is a failure/corrective action table applicable to the preferred embodiment of the present invention.

DETAILED DESCRIPTION OF THE INVENTION

Figure 1:
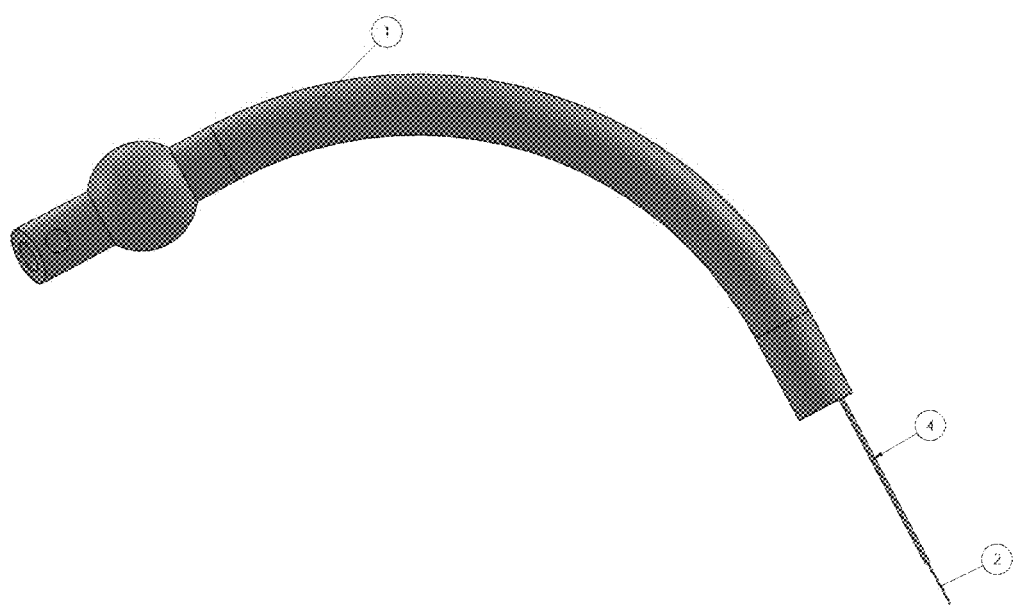
FIG. 1 shows one embodiment of the assembled inventive device, an endotracheal tube with wire leads protruding from the proximal end.

Ventilator associated pneumonia (VAP) is responsible for a large number of infections and deaths. There is currently no product available that is aimed at early detection of VAP, and very few are focused on prevention. The problem associated with this lack of devices is that as clinicians begin to recognize the symptoms of VAP, a substantial infection has already had time to develop. This leads to greater complications for the patient and higher antibiotic dosages and prescription lengths. All of these have huge social and economic impacts on the hospitals where this is occurring.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

It is contemplated that any method or apparatus described herein can be implemented with respect to any other method or apparatus described herein.

Design Overview

In certain embodiments, the probe for the inventive device will consist of four main components: 1) a modified endotracheal tube, 2) 35N LT wiring (Fort Wayne Metals, Fort Wayne, IN), 3) gold-plated electrode contacts, and 4) silicone tubing. The wires can connect an electrical subsystem to the contacts adhered to an inner surface of the endotracheal tube. The wires can be insulated from the environment by the silicone tubing until they reach the electrical subsystem, where data-gathering and analysis will occur. The signal sent to the sensor can be affected depending on the characteristics of the mucus and the frequency of the signal. The altered (phase shifted) signal can be sent back out of the endotracheal tube to a computer where it is compared to a control signal, and mathematical impedance formulas are used to determine the electrical impedance of the mucus at individual frequencies. Normalized resistance at low frequencies will be measured for changes which indicate the presence of VAP.

A preferred embodiment will be discussed below, but embodiments of the present invention are in no way limited thereto.

Materials for a preferred embodiment of the invention were selected as follows. A standard 7.5 mm endotracheal (ET) Tube (Dynarex® Endotracheal Tubes with Stylette, Cuffed, 7.5 mm; Dynarex Corporation, Orangeburg, NY) was selected as this is the standard size used for females when being intubated. This ensures that the inventive device will be able to fit in all adult sizes of ET tubes. 35N LT Wire (chromium/nickel/molybdenum alloy; Fort Wayne Metals, Fort Wayne, IN) was selected to connect the electrode to the electrical subsystem because of the biocompatibility, flexibility, small diameter, and similar applications including pacing leads, stylets, and catheters. Gold-plated electrodes were selected for the electrical system due to their commercially standardized values and well-documented behaviors in various systems. An Arduino Due (microcontroller board from Arduino, Lancaster, PA) was selected as the electrical subsystem as it best fit needs for the device. Ideally, there would be two lumens to house each lead traversing the wall of the ET tube to connect to a port where the electrodes would sit. This is feasible as the standard endotracheal tubes already have a lumen of the same size for inflating the pressure cuff of the tube. However, this would require a significant level of manufacturing capability. The work-around of encasing and adhering the leads on the inner surface of the ET tube for a prototype adds two more materials, standard silicone tubing (0.020 in ID/0.037 in OD) and Scotch-Weld Instant Adhesive (CA40H; 3M Corporation, St. Paul, MN). The silicon tubing was selected so that the leads are not exposed to the humidified airway of the patient. Silicon Tubing has many similar applications for encasing implantable leads. The Scotch-Weld Instant Adhesive was selected as it is considered a biocompatible adhesive which can be used to glue down the encased wires to the inside of the ET tube.

The design for the preferred embodiment will need to accommodate most ET tube designs and specifications. In order to ensure this, the Dynarex ET tube was selected because it possesses many features common to all ET tube models currently on the market. This part was purchased directly from a manufacturer, WorldPoint (Wheeling, IL). This tube is made with plasticized polyvinyl chloride (PVC), which is the current industry standard and signifies a major improvement over rubber ET tubes of the past. Additionally, this model has an important feature, the sub-glottal hole, which allows excess mucus accumulated against the distal side of the pressure cuff to be suctioned out more easily. Since the majority of ET tubes possess this feature, it was important to consider in the selection of the representative model. Lastly, the pressure cuff, external to the distal end of the endotracheal tube, is made of latex, which has high compliance, tensile strength, and elasticity. For these reasons, the latex pressure cuff is also a popular feature of the standard ET tube and is an important consideration for the design and implementation of a sensor such as the present one.

Material Selection for the wire connecting the electrode and ET tube system to the Arduino and CPU analysis system was based on finding materials that were standard in many applications in the medical field. The material selected is 35N LT because it has many similar applications such as pacing leads and catheters. 35 Gauge provided the minimal stiffness and a diameter ideal for the present device configuration and biological application.

Material selection and design of the electrodes prioritized signal acquisition and biocompatibility. Metal electrodes were selected to increase the signal acquisition and resolution potential of the design. In particular, gold-plated electrodes were selected for the relatively high biocompatibility of the surface interaction gold would have with the mucosal tissue of the trachea. If testing shows higher levels of biocompatibility are required, the gold electrodes can be coated with the biocompatible and hyper-conductive polymer polypyrrole (PPy). PPy has been used in many neural interface and micro electromechanical systems (MEMS) applications and will serve to increase the biocompatibility of the electrode configuration.

Figure 2:
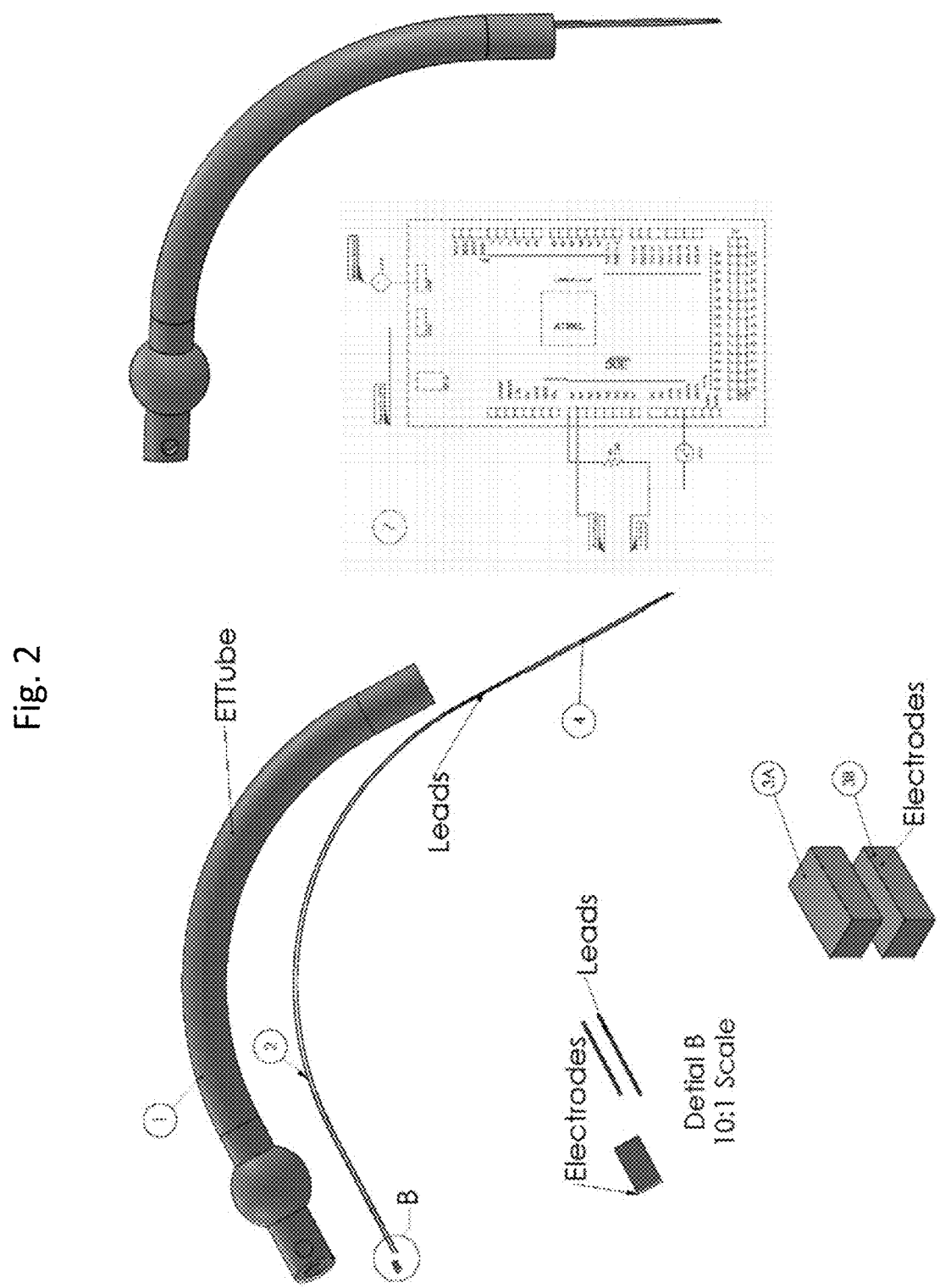
FIG. 2 shows the individual components of one embodiment of the inventive device and the probe circuit schematic for connecting to the Arduino microcontroller.
Figure 3:
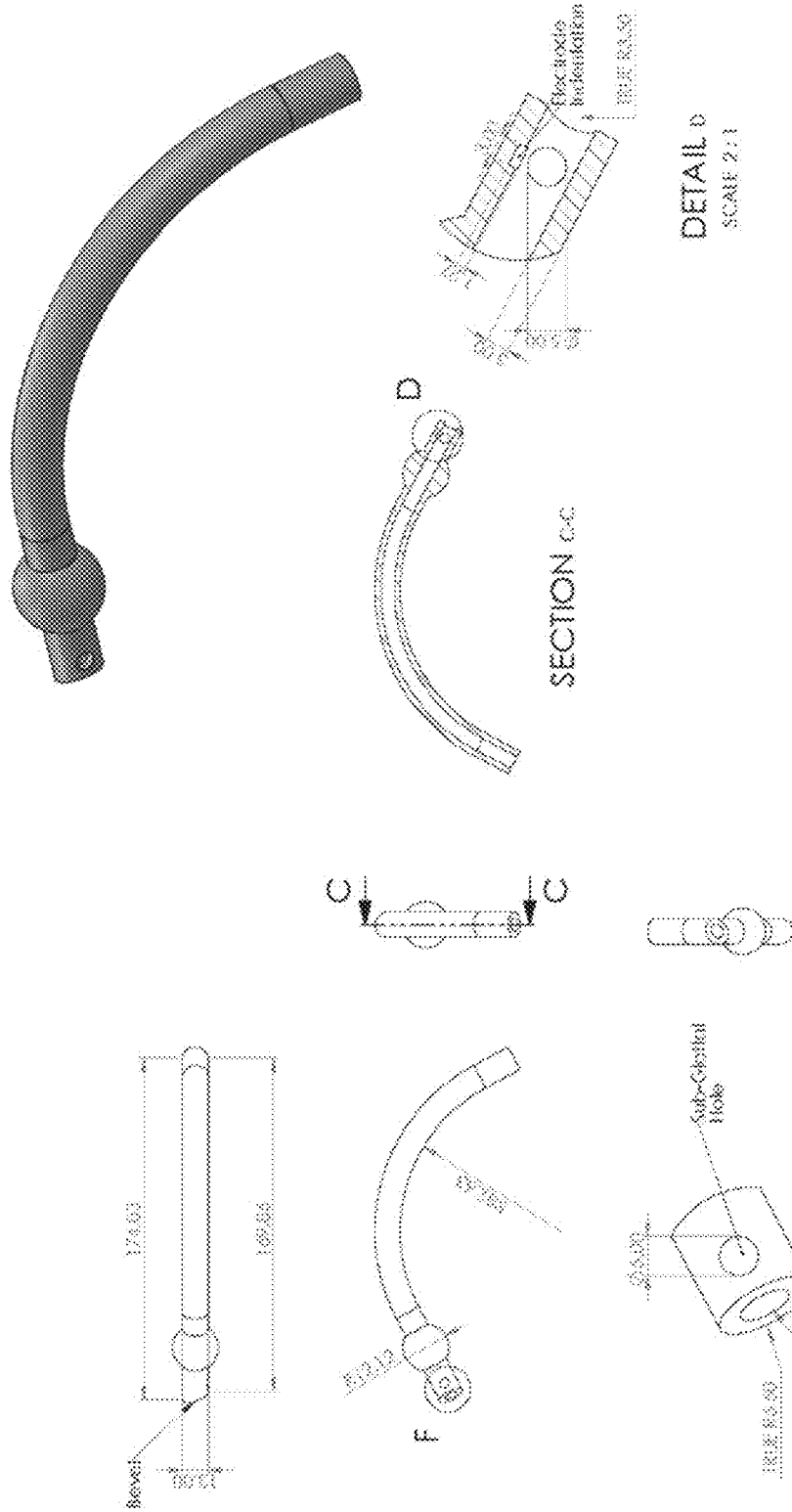
FIG. 3 shows dimensions of the endotracheal tube selected for one embodiment of the inventive device.
Figure 4:
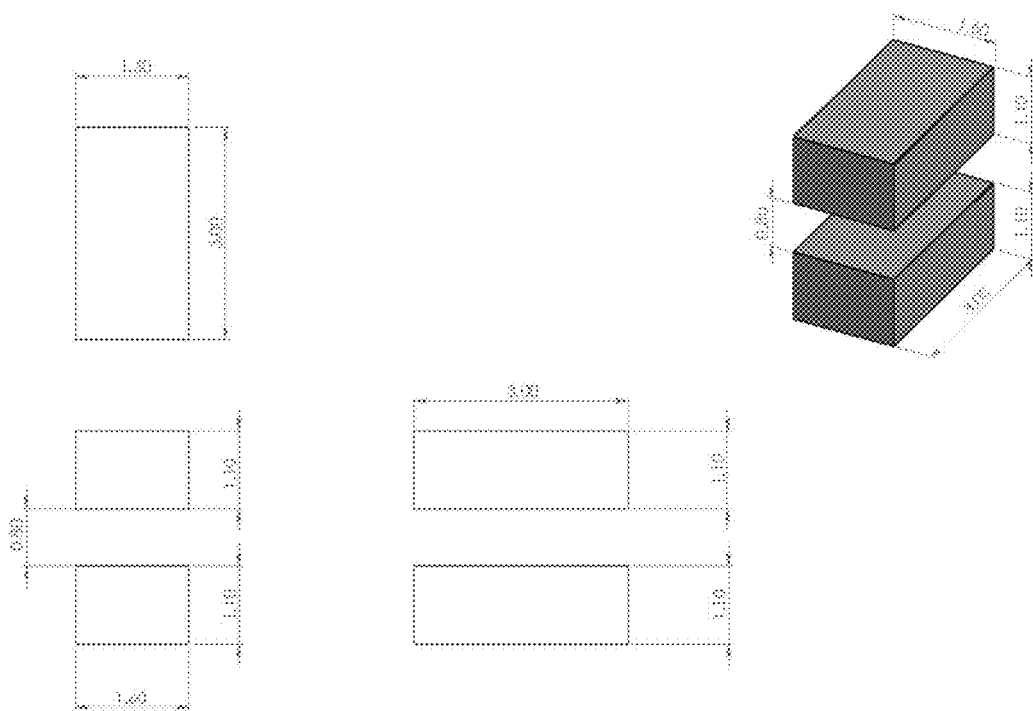
FIG. 4 shows dimensions of the gold plated electrode contacts selected for one embodiment of the inventive device.
Figure 5:
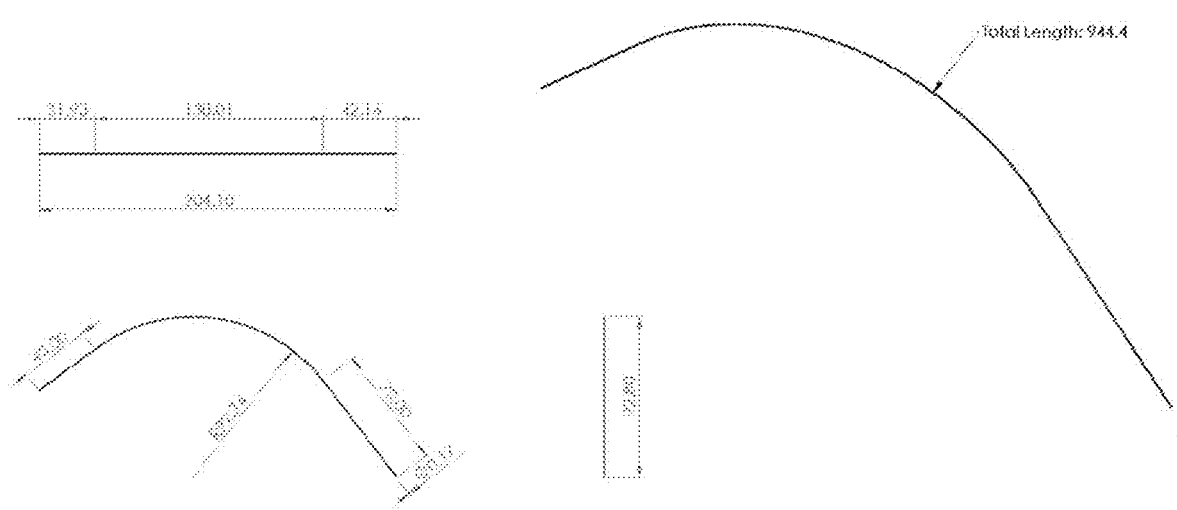
FIG. 5 depicts dimensions of the leads selected for one embodiment of the inventive device.
Figure 6:
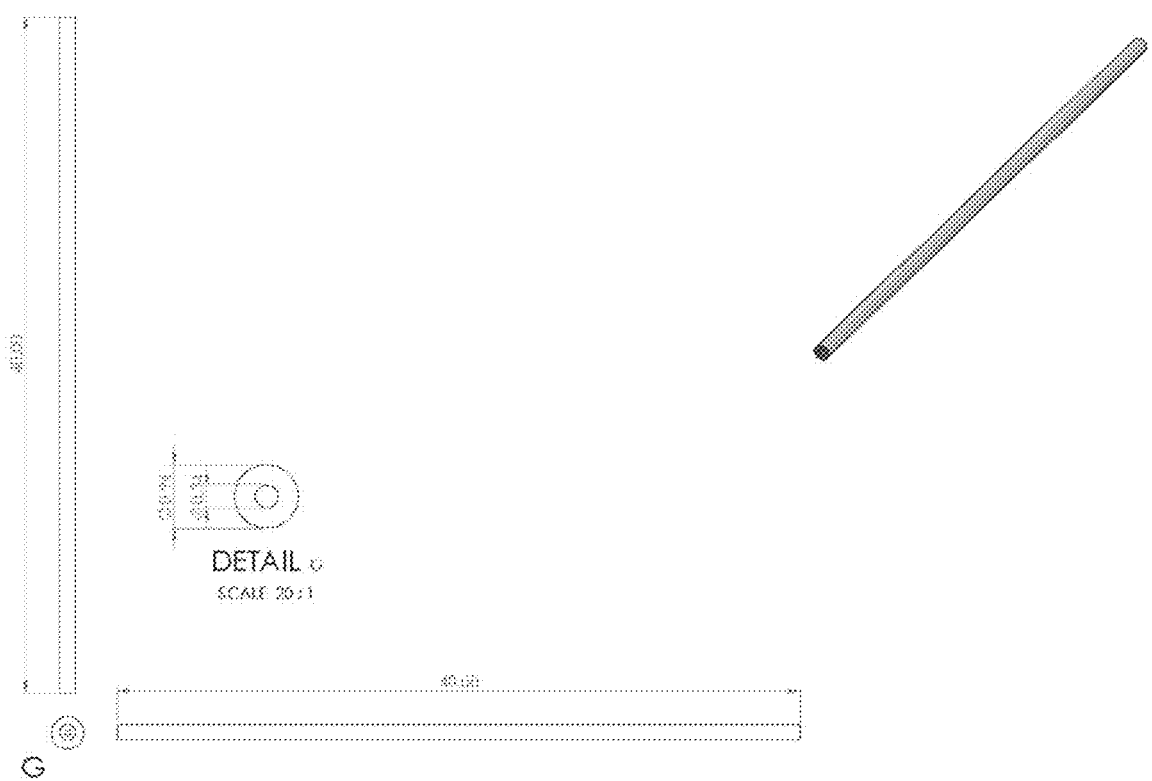
FIG. 6 depicts dimensions of the silicone tubing used to encase the leads for one embodiment of the inventive device.

A preferred embodiment of the inventive device is shown in detail in FIGS. 1-6. FIG. 1 shows endotracheal tube 1, with protruding leads 2 enclosed by silicone tubing 4. FIG. 2 additionally shows gold electrode contacts 3A and 3B as located in detail area B and the Arduino controller and probe circuit schematic 7 for this preferred embodiment. FIG. 3 shows more detail of the features of endotracheal tube 1. FIG. 4 shows dimensions of gold electrode contacts 3A and 3B. FIG. 5 shows dimensions for wire leads 2. FIG. 6 shows dimensions for silicone tubing 4 that encases wire leads 2.

Figure 7:
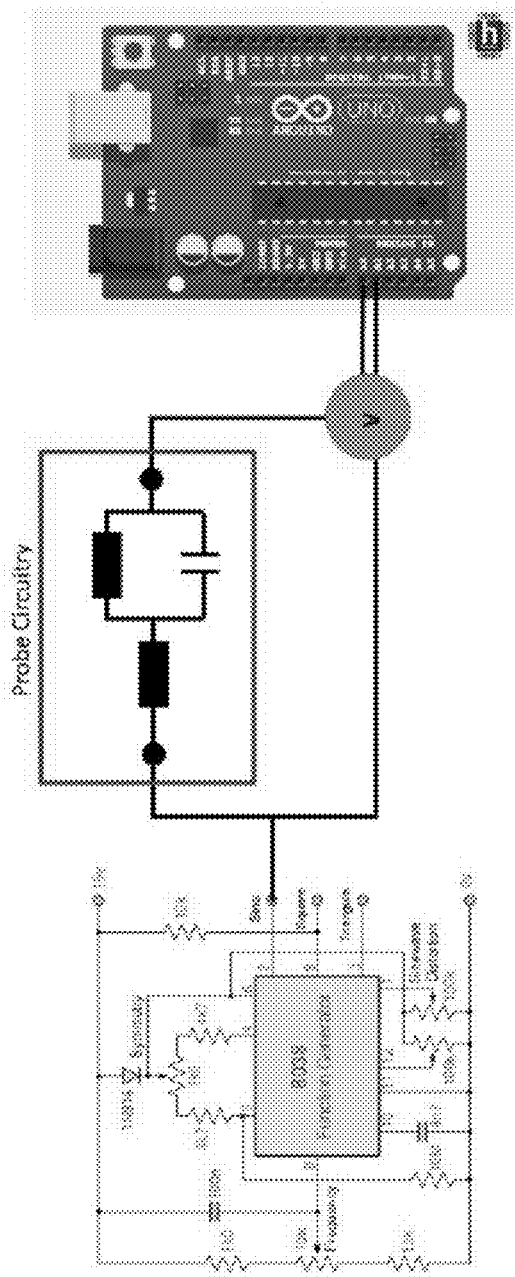
FIG. 7 shows the probe circuitry including a function generator and the Arduino board, with the electrode/mucus/electrode interface shown as a red box.

The circuitry schematic for the preferred embodiment of the inventive device is shown in FIG. 7. It describes the pathway from the function generator to the Arduino microcontroller. The split prior to probe is used to send an unaffected signal straight from the function generator to serve as a reference. The red box represents the mucus layer between the two electrical contacts. Signal intensities can be measured using the Arduino microcontroller. The microcontroller and/or an auxiliary computer can determine the impedance at the probe at each frequency of interest based on the values received from the probe and voltmeter. The impedance values can be combined into a spectrum for each time point recorded. Each spectrum can be compared against algorithms defined during testing in order to verify the presence and concentration of bacteria.

For some embodiments, silicon tubing was selected so that the leads are not exposed to the humidified airway of the patient. Silicon tubing has many similar applications for encasing implantable leads. The chosen tubing possesses an inner diameter of 0.02 inches and is therefore ideal for the 35N LT wire encapsulation, insulation, and protection.

The design of the subject electrochemical impedance sensor (EIS) uses mucus which accumulates at the distal end of the ETT and analyzes it for bacterial colonization using electrodes connected to a biosensor. See FIG. 2.

Signal Relay

The signal begins in the function generator then passes through silicone insulated leads into the ETT probe. Impedance characteristics of the mucus alter the current and amplitude of the signal. Two separate leads bring this signal into a protoboard for signal separation into waveforms representing current and voltage. The oscilloscope then receives the waveforms and calculates impedance values based on the frequencies, amplitudes, and phases measured. Normalized resistance and changes of phase at a range of frequencies are tracked for differences over time, which indicates the presence of VAP.

Electrode Placement

The leads connect the biosensor to the contacts adhered to the inner surface of the ETT as shown in FIG. 4. Alternate placements of the electrodes (such as on the interior of the pressure cuff and/or placement of a reference electrode set in the proximal end of the ETT) have been considered to reduce potential noise-to-signal ratio, but optimal placement of the electrodes was not testable due to the COVID-19 pandemic. Depending on the results of optimization testing, further embodiments of the device may include electrode placement not in the ETT tube itself, but in the suctioning system designed to periodically remove subglottal secretions from the end of the ETT. This would provide a more controlled environment for the sensor to operate in but would potentially limit the sensing frequency to the frequency of bronchoalveolar lavage, every 1-2 hours.

Mechanism of Action: Electrochemical Impedance Spectroscopy

Not wishing to be bound by theory, Applicants suggest that the following explanation may be helpful in understanding EIS. In alternating current (AC) circuits, voltage is affected by resistance as well as other additional factors. Capacitance and inductance are frequency-dependent properties which effect voltage. The combined effect of resistance, capacitance, and inductance is referred to as impedance. AC signals are often represented as sine waves. If a resistor (with an influence independent of frequency) is applied to this AC signal, then the amplitude of the sine wave is decreased proportionally to the resistance applied. However, if the circuit includes components such as inductors and capacitors, then not only is the amplitude changed, but the time at which the current flows in relationship to the voltage applied also gets translated horizontally. This translation in time is referred to as a "phase shift." EIS is the monitoring/measurement of both phase and resistance change in a system. This means substances are characterized not just by their resistance, but also by their capacitance and inductance, which allows EIS designs to blueprint complex systems much more accurately than ever before. EIS is a tri-variable assessment of a substance's electrical properties and can be used to differentiate between mixtures of differing concentrations.

Discussion of Functionality

Sensitivity

Sensitivity is one of the first concerns within the design of all biosensors. The pathological definition of infection in a brachial aspirate sample is $10^6$ colony forming units (CFUs) per mL. Kollef, M. H., *Silver-Coated Endotracheal Tubes and Incidence of Ventilator-Associated Pneumonia*. J. Amer. Med. Assoc. 2008, 300(7): 805; Vincent, J. L., et al., *The prevalence of nosocomial infection in intensive care units in Europe: Results of the European Prevalence of Infection in Intensive Care* (EPIC) Study, EPIC International Advisory Committee, J. Amer. Med. Assoc. 1995, 274(8):639-44. Fortunately, the sensitivity of electrochemical impedance sensors has been well documented for various purposes. For example, EIS systems have been used in battery development and corrosion characterization. More recently, investigators have started to utilize EIS for equally sensitive yet more biologically relevant systems such as water quality and food safety assessments.

However, EIS has not yet been used to characterize disease to any notable scale. In the research and laboratory setting, there is a foundation for developing a scalable EIS biosensing system for disease detection. In fact, one group investigated 3D printed carbon electrodes as an affordable model for detecting bacteria in medical settings. Ward, A. C., et al., *Identification and characterisation of Staphylococcus aureus on low cost screen printed carbon electrodes using impedance spectroscopy*, Biosensors and Bioelectronics 2018, 110:65-70. With this protocol, they were able to achieve sensitivity to the minimal concentration required to diagnose an infection, $1.8 \times 10^6$ colony forming units (CFUs)/mL. The present design improves upon the quality of the electrodes, and therefore a correlated increase in sensitivity can be expected. Even if testing should prove that these electrodes are inadequate, surface modifications have been shown in other applications to increase sensitivity to as much as 2 CFUs/mL and could yield useful embodiments. Barreiros dos Santos, M., et al., *Highly sensitive detection of pathogen Escherichia coli O157:H7 by electrochemical impedance spectroscopy*, Biosensors and Bioelectronics 2013, 45:174-180.

Specificity

False positive results were one of the primary complaints expressed by a physician during clinical interviews. In order to ensure specificity, not only must the device have high sensitivity and resolution, but this study's selected design utilizes a broad range of frequencies (1 Hz-100 MHz) to generate a comprehensive analysis of a sample's characteristics. Utilizing EIS through a variable frequency AC signal offers the advantage of generating a highly specific sample profile, such as those seen with other characterization techniques such as infrared spectroscopy. Ultimately, the specificity of the device will depend on data collection and characterization of interfering or confounding particulates, which may be enhanced using metrics from clinical or laboratory testing.

Biocompatible/Functionally Inert

Ventilators serve a vital role in patient care. No healthy patient is placed on a ventilator, and compromising the ventilator's function would be fatal. Therefore, this design has avoided placing any component of the system in a way that would pose a threat to ventilator function or create additional risk for the patient. The materials in direct contact with patient tissue are the same materials as any standard ETT to minimize potential biocompatibility complications, and the electrodes, while exposed to the mucus, obstruct less than 1% of the cross-sectional area of the ETT airway.

Short Testing Period

The generation of a single spectrum of impedance values across a given frequency range will be treated as a testing period. This period along with any interval between periods determines a testing frequency. An exemplary testing frequency is once per 24-hour period. Technical specifications dictated a testing frequency of one result per two-hour period. In preliminary testing, the average time required to manually collect this data across five frequencies within a range of interest and interpolate the values was less than 30 seconds. This time is expected to decrease with automation of the frequency sweep.

Passive Operation

For this device to effectively reduce hospital costs, the design must account for independent operation, without user interaction between the time of intubation and either extubation or infection. While the presently illustrated embodiment requires manual frequency adjustment to generate each impedance profile, the device can be automated to remove the need for input except at the above-specified times.

Specifications for the preferred embodiment are shown in Table 1:

TABLE 1

Specifications for a Preferred Embodiment

| Tech. Spec. ID | Description of Specification | Meets Requirement? |
| --- | --- | --- |
| TS-001 | Specificity score greater than 90% (True Negative/(True Negative + False Positive) | This would need to be tested, but multiple research papers have indicated that many bacterial strains, including *Staphylococcus Aureus*, show an impedance measurement directly related to concentration at a different frequencies. |
| TS-002 | Sensitivity score greater than 90% (True Positive/(True Positive + False Negative)) | This would need to be tested, but multiple research papers have indicated that many bacterial strains, including *Staphylococcus Aureus*, show an impedance measurement directly related to concentration at a different frequencies. |
| TS-003 | Fits on/inside endotracheal tubing ranging from 2 mm-10 mm (Pediatric-Adult sizes)(If solution warrants this placement) | There are wires available that should fit on the inside of all ranges of tubing. The electrode distance and surface area would need to be recalculated to determine electrode feasibility in tubes with an inner diameter less than 7 mm. |
| TS-004 | Conform to ISO 10993 standards for confirmation of biocompatible status | Full biocompatibility will need to be tested following device prototyping however the probes only come into contact with the endotracheal tube and secreted mucus, there is no direct interface between the body and probes. |
| TS-005 | Maximum time per test will be under 2 hours | This test is continuous, but does require a normalization measurement to be taken from the very beginning. Full spectrum can be determined in less than a few minutes |
| TS-006 | Ventilator will continue to deliver optimal concentration of oxygen despite the solutions attachment (O2 saturation between 92-98%) | The placement of the electrode, hydrophobic ring, and wires will be located inside the tube with only the electrode and hydrophobic ring being exposed to the airflow. The sensor is in line with the tube which means normal airflow/oxygenation should continue. |

TABLE 1-continued

Specifications for a Preferred Embodiment

| Tech. Spec. ID | Description of Specification | Meets Requirement? |
|---|---|---|
| TS-007 | Solution will be compatible with all ventilator modes: VC-AC, VC-MMV, PC-CMV, PC-SIMV-SIMV, PC-AC, PC-APRV, PC-PSV, SPN-CPAP/PS, SPN-CPAP/VS, SPN-CPAP, and SPN-PPS | The placement of the electrode, hydrophobic ring, and wires will be located inside the tube with only the electrode and hydrophobic ring being exposed to the airflow. The sensor is in line with the tube which means normal airflow/oxygenation should continue. |
| TS-008 | Simple GUI, follows the 10 Heuristics for User Interface Design? | The GUI will be made from scratch to meet the requirements. |
| TS-009 | Device parts are easily attached/detached to/from current ventilator system | The device is built into the endotracheal tubing and only needs to be plugged into a signal generator and the alert system. Otherwise the system very easily attached/detached. |
| TS-010 | Device as a whole is user friendly for all medical personnel (doctors, nurses, first responders, etc.) | The device is built into the endotracheal tubing and only needs to be plugged into the signal generator and arduino for analyzing. After powering on, device will operate completely on its own |
| TS-011 | User interaction only required during setup and device removal | User interaction will be required for intubation before and removal of the endotracheal tube. The only other time user interaction is required is when the sensor is indicated concentrations of bacteria being present and a medical personal is needed to check the patient. |

Assembly instructions for the preferred embodiment are as follows:

1. Purpose

The purpose of this section is to specify the assembly instructions and the tools required to build the inventive device.

2. Scope

This procedure is applicable to for the assembly of the inventive device

3. Responsibility 3.1. A trained and qualified manufacturing personnel is responsible for the overall assembly.

3.2. Quality and Manufacturing are responsible for inspecting and verifying the acceptance criteria.

4. Reference Documents 4.1. Part Drawings

5. Definitions 5.1. ET Tube Features 5.1.1. Distal End of ET tube: Refers to the end of the tube that is inserted into the trachea and has the balloon cuff and subglottal hole 5.1.2. Proximal end of ET tube: Refers to the end of the tube that is on the opposite side 5.1.3. Pressure Cuff: The pressure cuff, also called balloon cuff, is the key feature of the ET Tube for adults. Once inflated, the cuff acts as a seal for the trachea so that positive pressure cannot escape from the lower airway as well as seal the upper airway.

5.1.4. Subglottal hole: Opening on the distal end of the tube that provides a place to suction built up mucous 5.2. Blade No. 11: The No. 11 blade is an elongated blade sharpened along the hypotenuse edge. It has a strong pointed tip making it ideal for stab incision.

TABLE 2

Equipment and Materials Required for Assembly and/or Testing

| Part/Tool# | Tool and/or Material Description | Size/Quantity |
|---|---|---|
| Part No. 1 | Dynarex ® Endotracheal Tubes with Stylette, Cuffed, 7.5 mm | 1 |
| Part No. 2 | 35 NLT Wire | Diameter: 0.17 mm Length: 3 ft Quantity: 2 |
| Part No. 3 | Gold-plated Electrode | 1 |
| Part No. 4 | Standard Silicone Tubing (0.020 in ID/ 0.037 in OD) | 3 ft. length (2 needed) |
| Part No. 5 | 3M ™ Scotch-Weld ™ Instant Adhesive CA40H | 1 oz |
| Part No. 6 | 1K Ohm Carbon Film Resistor | 1 |
| Part No. 7 | Arduino Due | 1 |
| TL- 1 | Shard ™ Premium Stainless-Steel Surgical Scalpel Blade No. 11 | 1 |
| TL - 2 | Meter Stick | 1 |
| TL - 3 | Vernier Caliper | 1 |
| TL - 4 | Wire Cutter | 1 |
| TL - 5 | Wire Stripper | 1 |
| TL - 6 | Soldering Iron | 1 |

7. Safety Precautions

Follow standard PPE procedure during product assembly.

8. Procedure/Assembly Instructions

This section will give general assembly instructions, specific sub assembly instructions, and detailed full assembly instructions.

8.1. General Assembly Instructions:

Since the inventive device consists of multiple parts, each part is to be obtained and assembled separately and then put together during the final assembly. The first step to assemble our device is to get the parts and material specified above in section 6. Using a small scalpel, indent a cube 1.4 mm deep, 3 mm wide, and 3 mm long into the endotracheal tube approximately 2 mm from the distal end (side with the balloon pump) and 90*(+/−2 rotated clockwise from the subglottal hole. See FIG. 3.1 for reference. Confirm dimensions with a Vernier caliper before continuing. The tolerance for these dimensions is +/−0.50 mm. Next, two pieces of silicon tubing will be measured and cut to approximately 3 ft. (+/−1/32 in) each. The silicon tubing will then be adhered with 3M™ Scotch-Weld™ Instant Adhesive CA40H to the inside of the Endotracheal Tube approximately 90° rotated clockwise from the subglottal hole and approximately 5 mm from the distal end. The silicon tubing should match up with the side of the indentation perfectly. Then, measure and cut two pieces of the 35 NLT wire to be approximately 3 ft (+/−0.5 in) each. Strip approximately 1 cm (+/−1 mm) on both the distal and proximal ends of the 35 NLT wire. Using a soldering iron, solder the distal end of one wire to one of the gold-plated electrodes. Repeat this step for the other wire. Next, guide the soldered 35 NLT wire and electrode through the silicon tubing from the distal end to the proximal end. The electrode should fit nicely into the indented cube created in the first step. Then, solder the wires to the PCB accordingly.

8.2. Detailed Part Instructions 8.2.1. Endotracheal Tube Modifications 8.2.1.1. Use a clean #11 blade scalpel to make an indentation approximately 1.4 mm deep, 3 mm wide, and 3 mm long into the endotracheal tube approximately 2 mm from the distal end (side with the balloon pump) and 90* rotated clockwise from the subglottal hole.

8.2.1.2. The purpose of this indentation is to serve as a holder for the electrodes in the final assembly.

8.2.2. Silicon Tubing 8.2.2.1. Using a meterstick and the same scalpel above, measure and cut the 0.02 in ID silicon tubing to approximately 3 ft. (+/−0.5 in.)

8.2.2.2. Ensure the cut is as straight as possible, clean cut, and there are no fragmented pieces of silicon left.

8.2.2.3. Repeat steps 8.2.2.1-8.2.2.3 to produce a second silicon tubing 8.2.3. Leads 8.2.3.1. Measure and cut the length of the 35 NLT wire to be approximately 3 ft. using a meter stick and wire cutters.

8.2.3.2. Ensure the cut is a clean cut and the wire is not frayed 8.2.3.3. Repeat steps 8.2.3.1-8.2.3.3 to produce a second wire 8.2.3.4. Using a wire stripper, strip approximately 1 cm (+/−1 mm) of each the proximal and distal ends of both wires 8.2.4. Electrodes 8.2.4.1. Using wire cutters, cut the gold-plated electrode to be 1.6×3 mm 8.2.4.2. Do this twice so there are two electrodes 8.3. Detailed Full Assembly of the inventive device (After Individual Part Assembly)

8.3.1. Place the measured and cut Silicon Tubing in the Endotracheal Tube 5 mm from the distal end of the ET tube and 90 degrees clockwise from the subglottal hole. The measured and cut Silicon Tubing is to be adhered to the inside wall of the Endotracheal Tube in the previously mentioned position with 3M™ Scotch-Weld™ Instant Adhesive CA40H. The tubing should meet the edge of the indentation made in step 8.2.1.1. Hold the Endotracheal Tube at an angle in which the Instant Adhesive will be able to drip down the tube. Once the entire Silicon Tubing has been coated with the Instant Adhesive, wait 10 minutes to dry. Repeat Step 8.3.1 with the second Silicone Tubing.

8.3.1.1. Visual and Quantitative inspection is to be performed by each member of Tera BioTech to make sure proper placement of the Silicone Tubing inside the ET tube has occurred.

8.3.2. Using a soldering iron, solder the stripped part of the distal end of the measured, cut, and stripped 35 NLT wire to the measured and cut gold-plated electrode. Repeat Step 8.3.2 with the second wire and gold-plated electrode. 8.3.2.1. Visual inspection of the solder is to be performed by each member of the Tera BioTech team.

8.3.3. Using tweezers, thread the lead and electrode assembled in step 8.3.2 through the Silicon Tube that is adhered to the inner wall of the ET Tube. Repeat this step with the other lead/electrode and tubing. If done correctly, the gold-plated electrode will fit perfectly into the premade indentation in the ET tube created in step 8.2.1.1. 8.3.3.1. Visual inspection of the lead and electrode placement is to be performed by each member of the Tera BioTech team 8.3.4. Insert the proximal end of the lead into the Arduino ports describe in the electrical subsystem below.

9. Tests for Correct Assembly 9.1. Preliminary Calibration Testing 9.1.1. Before implanting the circuit components (Parts 2,3,7) into the ET tube or silicone protective tubing place the contacts of the carbon filament resistor (Part 6) on each electrode.

9.1.2. Run the system and ensure you observe a corresponding loss of signal proportional to the applied resistance.

9.2. Final pre-testing protocol 9.2.1. Place contacts of the carbon filament electrode (Part 6) on each of the electrodes when embedded in their proper positions inside the endotracheal tube following assembly instruction steps 8.3.4

9.2.2. Repeat Step 9.1.2 with the full system setup.

10. Quality Inspection/Acceptance Criteria

The Completed PneuMed device will have to pass both a visual inspection by each member of the TeraBioTech team and the mentors of the team, as well as pass the tests for correct assembly listed in section 9.

11. Records

Ensure proper documentation and records are held in the Senior Design 2 binder of all protype builds and tests completed.

Electrical Subsystem

The Arduino Due system is used in this set-up for all signal generation and processing. The device is powered using a micro-usb connection into a battery pack with a minimum supply of 3.3V. The electrical probe is to be connected to the Arduino using leads into DAC0 and A1 as seem in FIG. 6. The reference pathway leads into ports DAC0 and A0, FIG. 6. In the prototype version of the sensor, calculations are qualitative and are used to determine a rough electrical impedance spectrum of the specific material measured by the probe. Manufactured models of the sensor will use the USB port as seen in FIG. 6 to send data to a local CPU to compare to known spectrums stored on the computer using MATLAB.

Signals are generated using the Arduino Due's onboard digital to analog converter. The Arduino is capable of producing sine-shaped waveforms using a DC supply with a minimum value of 0V and a maximum of 3.3V. These waveforms are generated at specific frequencies according to the delay of the loop used in their production. After every period, the delay of the loop is increased to increment the frequency, with a range of 1 Hz to 100 kHz. The signal is then split between the reference pathway and the probe pathway. The signal is then received by the Arduino Due's analog to digital converter and stored in the flash memory of the device. The relative voltage drops into the two inputs are compared and plotted as the frequency of the output signal changes. This plot becomes the qualitative spectrum for the material analyzed by the probe and displayed on the local CPU using the usb port.

FIG. 8 shows the Arduino code for generating waveform and supplying to electrical probe and through a reference pathway and comparing the two values to determine profile of material at the end of the probe.

Testing

A probe setup using the function generator and arduino analysis system will be built in order to verify the theoretical calculations.

The system will be first tested with no solution between the probes to make sure control inputs and outputs are being formed and read properly by the system. After this is proven to be accurate testing using phantom bacteria solutions at small volumes will be performed. This will allow verify that the device is sensitive enough to recognize small changes in concentration and that the EIS spectrum is being formed properly. Following success in this test, the device will move onto the next stage of building and product testing for efficacy and safety.

Product Testing:

For our product, preferred embodiment PneuMed, product testing and analysis will be conducted as the device is being fabricated and assembled. Verification, validation, and safety testing are the main methods of testing that will be conducted to ensure that the device captures the customer needs, the device's software meets requirements, and that our device is safe for customer and patient use. Some of the standards from the joint technical committee of the International Organization (ISO) for Standardization and the International Electrotechnical Commission (IEC) that will be followed for testing are shown in Table 3[ref]:

TABLE 3

Standards for Testing

| Number | Name | Description |
|---|---|---|
| IEC 60601-1-11: 2015 | Medical electrical equipment Part 1-11: General requirements for basic safety and essential performance | This applies to basic safety and essential performance requirements for multifunctional patient monitoring systems that are used by medical professionals in healthcare facilities and emergency medical environments. |
| IEC 82304-1: 2016 | Health software Part 1: General requirements for product safety | This applies to the safety and security of software products designed to operate on general computing platforms without a dedicated hardware. This covers the entire lifecycle including design, development, validation, installation, maintenance, and disposal of health software products. |
| IEC 80416-1: 2008 | Basic principles for graphical symbols for use on equipment Part 1: Creation of graphical symbols for registration | This provides basic principles and guidelines for the creation of graphical symbols for registration which could be applied to our device. |
| IEC 62366-1: 2015 | Medical devices Part 1: Application of usability engineering to medical devices | This applies to the specific process for a manufacturer to analyze, specify, develop, and evaluate the usability of a medical device as it relates to safety. This also allows for a manufacturer to evaluate the usability of human factors and engineering to mitigate risks associated with correct and normal use. |
| IEC 60601-1-8: 2006 | Medical electrical equipment Part 1-8: General requirements for basic safety and essential performance | This specifies the basic safety and essential performance requirements and tests for alarm systems in medical devices and equipment to provide guidance to their application. This is accomplished by defining the alarm categories (priorities) by degree of urgency and their marking for all alarm types/systems. |

Figure 11:
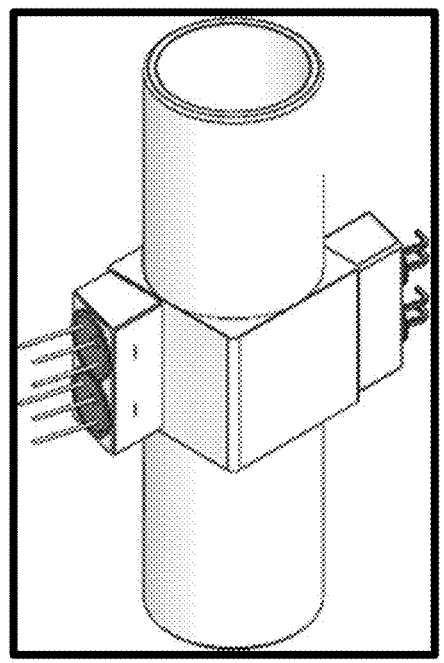
FIG. 11 shows an exemplary design for a mid infrared optical sensor to be fitted to an exterior portion of a tube carrying a patient's exhaled breath.

In certain embodiments, the inventive device can further include an infrared optical sensor for detecting ethanol and/or other gases of interest. An exemplary infrared biosensor design, illustrated in FIG. 11, includes 4 components: 2 infrared light sources, a linear multipass absorption cell, and a detector. The device itself would be inserted into the ventilator tubing immediately distal to the y-split where exhaled breath passes from the patient to the environment or a collecting chamber. Dispersive light is focused from the infrared source placed on the exterior surface of the exhaled-breath tubing into the multipass absorption cell inside the tubing where the light would interact with the patient's breath. The multipass cell serves to increase the path length of the light and therefore the amount of interaction with molecules in the breath; this allows for a higher sensitivity to be achieved. The light will pass back out of the tubing and into the detector where the absorbances of the separate wavelengths are measured. The output signal would be sent to a computer module for display and comparison to reference values.

The exemplary design utilizes 3.0 μm and 3.4 μm light sources to quantify the C—H and C—O bonds present in the exhaled breath and elucidate the presence of ethanol, a known biproduct of bacterial metabolism. The path length of the infrared light through the sensor is 5.7 cm, comparable to pathlengths in similar sensors. Popa, D., et al., *Towards Integrated Mid-Infrared Gas Sensors*. Sensors, 2019. 19(9): 2076. This is achieved by directing the light entering the sample cell at an angle of 15.5 degrees. 98% of the light is transmitted through each of the silicon windows and 96% is reflected off the gold-plated mirrors. Full strength signal of the detector receiving light from the 3.0 μm source was 0.36V. The detector for the 3.4 μm infrared light outputs 0.82V with no gas interference. With a basic computational sensor, this results in a high-resolution output read from the 3.0 μm source and 170 for the 3.4 μm source. This is sufficient for determining a change in gas present in exhaled breath but is limited by the quality of light sources or detectors.

Figure 12:
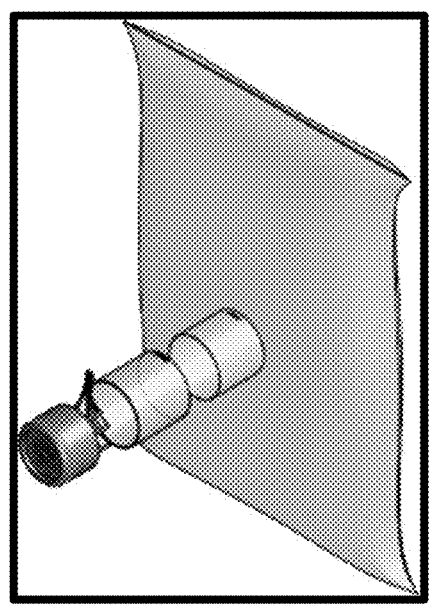
FIG. 12 illustrates one embodiment of a semiconductor gas sensor attached to a Tedlar gas collection bag for collecting a patient's exhaled breath.

In certain embodiments, the inventive device can further include a semiconductor gas sensor for sensing ethanol and/or other gases, such as the one illustrated in FIG. 12. An exemplary semiconductor design includes seven components including an MQ3 ethanol sensor (Huaban, Hangzhou, Zhejiang, China), a fixture component, a Tedlar bag (NuTech Instruments, Inc., Plano, TX) to collect the expired gas, six leads connecting the sensor to the printed circuit board (PCB), the PCB, an alarm system, and a graphic user interface. The MQ3 sensor is placed in the fixture that connects the bag to the expiratory limb of the ventilator. The fixture will have an opening to allow for the leads from the sensor to connect to the PCB. This establishes power for the sensor by connecting the 5V and ground (GND) terminals respectively. The other two connections are the analog and digital outputs of the sensor. When exhaled air flows through the expiratory limb of the ventilator, it will be collected in the Tedlar bag. The MQ3 sensor will be able to continuously read the amount of ethanol present. When the ethanol concentration reaches 1 mg/L, the alarm will alert a healthcare professional.

Figure 13:
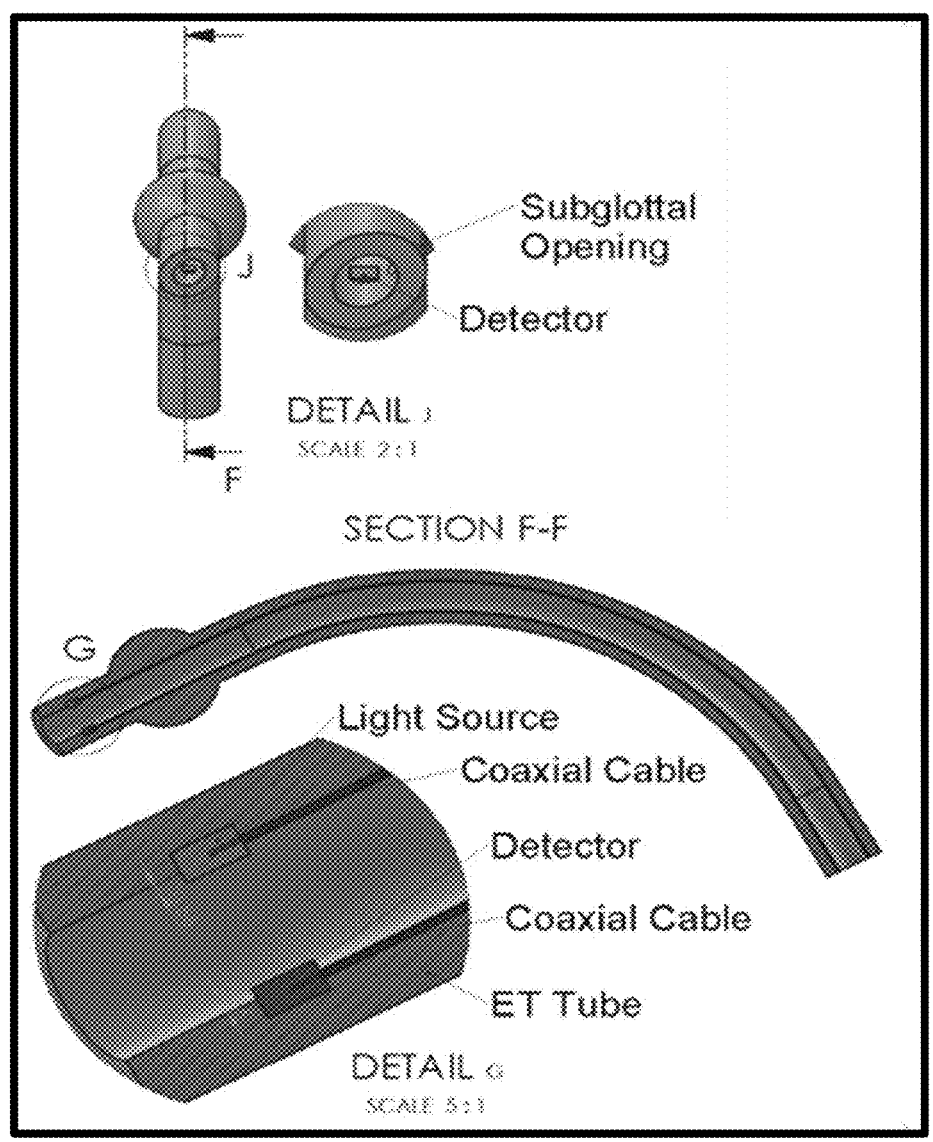
FIG. 13 illustrates one embodiment of a sectional view of an optical mucus sensor.

In certain embodiments, the inventive device can further include an optical mucus sensor. An exemplary design, illustrated in FIG. 13, would propagate a beam of visible light transversely across the intraluminal space of the patient's endotracheal tube. Upon crossing the space, the light would shine on a photocell which would generate an electrical current, which would be translated into a digital signal. The intensity of light interacting with the detector would be directly proportional to the current supplied to the system, and a voltmeter would transmit this data to a user interface such as an LED alert system.

To generate clinically relevant data, this device must detect changes in the amount of purulent mucosa present distal to the ETT cuff. Since purulent mucosa is characterized as "green-yellow" in color, it would attenuate this light frequency more than clear, white, or cream-colored mucosa, which have been strongly associated with absence of microbial content. Johnson, A. L., et al., *Sputum color: potential implications for clinical practice*, in Respiratory Care 2008, p. 450+. The photocell selected would generate 3.5 mA of current per lumen. With a high-resolution voltmeter, the system sensitivity is adequate to measure a variable biological target.

Regarding these optional additional sensors, placing components in the ETT presents a unique challenge of maintaining the conditions of oxygen delivery to the patient despite changes in the interior surface of the ETT to accommodate the source and sensor. In the exemplary illustrated preliminary designs, both additional components obstruct <2% of the ETT cross-sectional area.

Risk Analysis

Failure Mode and Effects Analysis (FMEA) is a design tool that is used to help mitigate risk in the design process prior to the prototyping phase. It is a structured approach which allows for the identification of possible failure modes along with their cause, effect, and significance. Risk Priority Number (RPN) is the product of the three variables probability of failure occurrence (OCC), failure severity (SEV), and failure detectability (DET). Each of these variables is measured using the scoring methodology discussed below.

TABLE 4

Failure occurrence (OCC) scoring methodology

| Failure Occurrence (OCC) Scoring Methodology Rating | Approximate Probability of Failure (per hour) | Description of Occurence |
| --- | --- | --- |
| 1 | ≤1 × 10−5 | Extremely Remote |
| 2 | 1 × 10−5 | Remote, very unlikely |
| 3 | 1 × 10−4 | Very slight chance of occurence |
| 4 | 4 × 10−4 | Slight chance of occurence |
| 5 | 2 × 10−3 | Occasional occurrence |
| 6 | 1 × 10−2 | Moderate occurrence |
| 7 | 4 × 10−2 | Frequent occurrence |
| 8 | 0.20 | High occurrence |
| 9 | 0.33 | Very high occurrence |
| 10 | ≥0.50 | Extremely high occurrence |

TABLE 5

Failure severity (SEV) scoring methodology

| Rating | Severity Description |
| --- | --- |
| 1 | The effect is not noticed |
| 2 | Very slight effect noticed, does not annoy or inconvenience patient |
| 3 | Slight effect that causes patient annoyance, but they do not seek assistance |
| 4 | Slight effect, patient may seek assistance to fix problem |
| 5 | Moderate effect, patient requires immediate assistance |
| 6 | Significant effect, causes patient dissatisfaction, may violate regulation or design code. |
| 7 | Major effect, system/device may not be operable, elicits patient complaint, may cause injury |
| 8 | Extreme effect, system/device is inoperable and a safety problem, may cause severe injury |
| 9 | Critical effect, complete system/device shutdown. Safety risk |
| 10 | Hazardous, failure occurs without warning, life threatening |

TABLE 6

Failure Detectability (DET) Scoring Methodology

| Rating | Description of Detection |
| --- | --- |
| 1 | Near certain to detect |
| 2 | Very high chance of detection |
| 3 | High chance of detection |
| 4 | Moderately high chance of detection |
| 5 | Medium chance of detection |
| 6 | Low chance of detection |
| 7 | Slight chance of detection |
| 8 | Remote chance of detection |
| 9 | Very remote chance of detection |
| 10 | No chance of detection |

Once each failure mode and their scoring for their OCC, SEV, DET, and RPN is determined a corrective action is then created. For each failure a new action is taken if it is within the scope of the device. If the action item needed to be taken is outside of this scope, it is listed as not applicable for our device. For example, how often a patient is moved around the hospital cannot be determined to a specific amount as each patient has different needs.

FIG. 9 shows a failure/corrective action table.

Figure 10A:
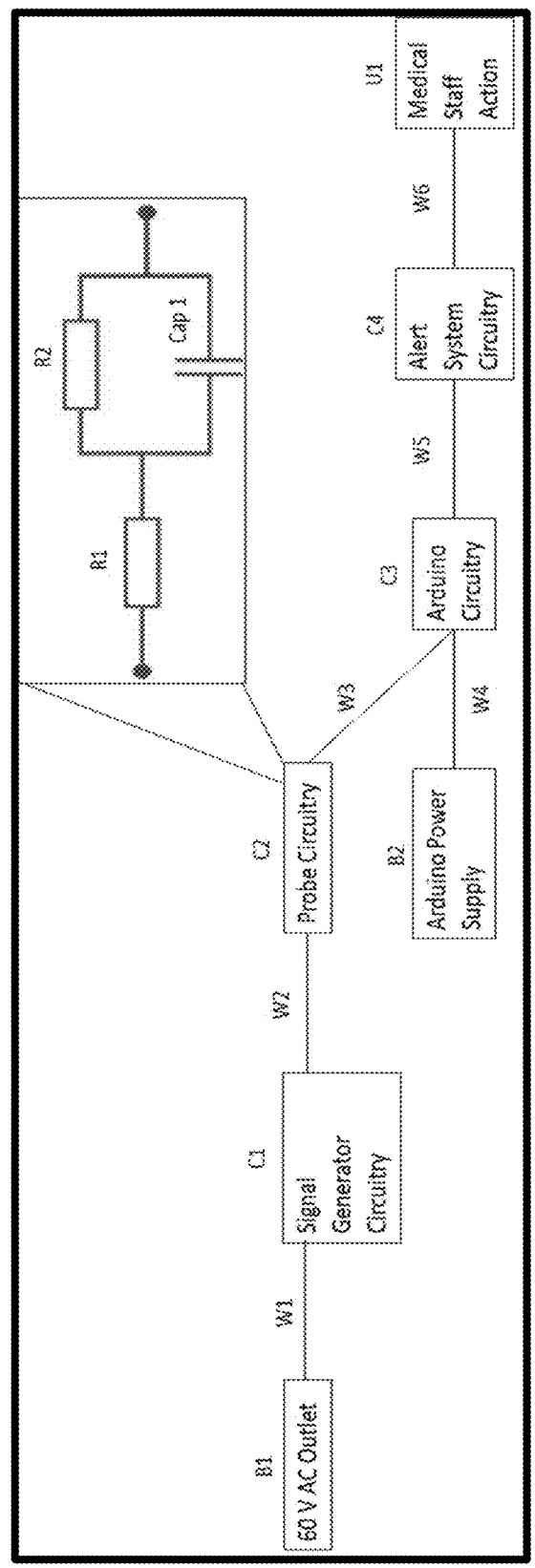
FIG. 10A shows the systemic circuit scheme for the preferred embodiment of the present invention.
Figure 10B:
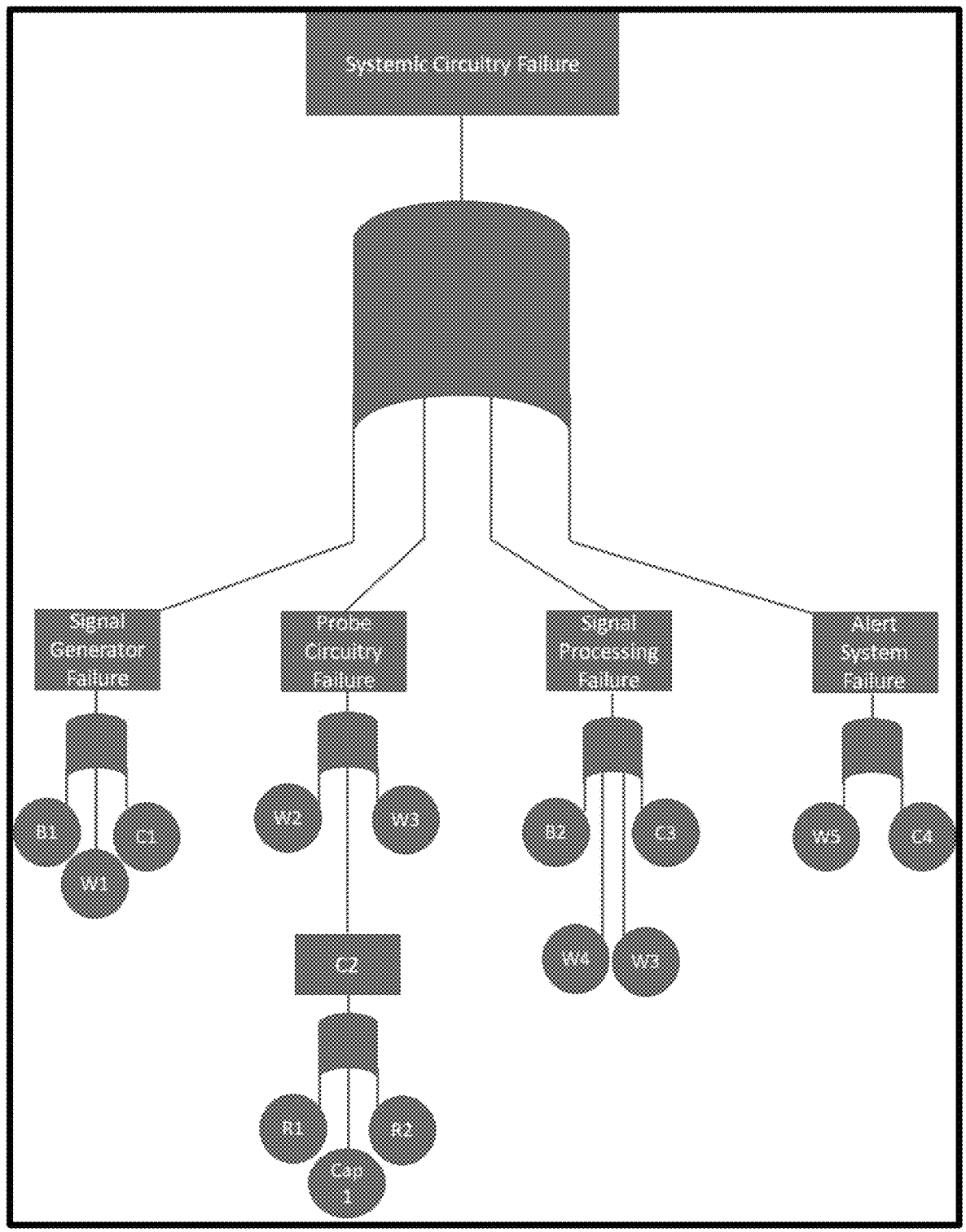
FIG. 10B shows the systemic circuitry failure scheme for the preferred embodiment of the present invention.

An overall system circuit diagram for the preferred embodiment is shown in FIG. 10A. The corresponding systemic circuitry failure scheme is shown in FIG. 10B. As described above, the proposed system will have many components. The signal generator will be powered by a standard wall outlet, and 60 V AC adapter power cable. The signal will be transmitted to the probe via coaxial cables. From the probe, the signal will be transmitted by coaxial cable to the Arduino processing circuit, the alert system, and to the attention of medical staff if necessary.

Within the probe itself, there are three main components that may fail. The control resistor (R1), which controls the total current in the system, the Capacitor (Cap 1), which will be created using the electrodes described above separated by the biological analyte (mucosa), and the constant resistor (R2), which will provide a pathway for current to flow when the impedance of the analyte is high, preventing charge accumulation in the electrodes.

Inherent Risks and Resolutions

Overall the total risk priority number (RPN) prior to taking any action was 2096. After taking action to reduce the total RPN of each component, the RPN was reduced to 1304 or reduced by 37.79%. It can also be noted that the RPN values for the endotracheal tube were not reduced at all. This was due to possible movements of patients that cannot be controlled by the device, and it is assumed that all medical professionals moving patients are trained to do so properly without affecting the endotracheal tube. If movement were to occur that affected the tubing it would not be on the device to account for it. If the RPN percent change excluded the endotracheal tube RPN values the percent change would instead be 58.41% decrease in RPN values. Each independent component's risk and resolution is further described below.

Endotracheal Tube
Risk:

Since our device is being incorporated into the endotracheal tube that is currently used on the market, there are multiple inherent risks associated. One of the most critical potential failure modes of the endotracheal tube is if airflow is blocked or altered, due to surgical misplacement of the tube, chemical degradation, and change in body position, causing severe risk to the patient. The other risk associated with the endotracheal tube is that if the PVC lining is ruptured, the components of our device could potentially be dislodged resulting in a loss of signal.

Resolution:

There is no corrective action that the team can implement in the device itself. The main focus to mitigate risk for the endotracheal tube is to ensure proper surgical technique when placing the ET tube and limit the amount of time the patient is moved. The material selection is also important because the added stiffness of our components in the ET Tube cannot affect the stiffness of the tube.

Signal Generator
Risk:

The main cause of concern for the signal generator is the output being different than expected either from the beginning or changing with time. If the signal is different than we have planned on from the start then the program run for analysis will be calculating results against an unfit control. The program will need to be time based so if the changing frequencies are occurring at the wrong time points then results will be incorrect and provide no insight to the detection of VAP. If the signal intensity is off from what is expected then the predetermined scale that describes the amount of change in mucus characteristics will be inaccurate and the sensitivity of the system will change. Changes in output signal due to continuous running of the signal generator also present a problem since the baseline will be determined using a different input than later tests.

Resolution:

Changes in the signal over time are controlled by the signal generator itself, the technical specifications allow for a 2% change in amplitude and 0.2% change in frequency. These values are inherent constraints of the system and will have to be taken into consideration when writing the program for analysis. In order to determine whether the system is working properly from the beginning, we will have a control test cycle that calculates the amplitude and sweep time of the signal generator prior to beginning testing of mucus. If the values are off from what is expected, then the program will not run and will recommend checking proper setup of the signal generator to the user.

35N TL Wires
Risk:

The function of the 35N TL wires is to connect the electrode to the signal generator. The risk associated with these wires is that the connection between components is lost. This would cause the device to lose communication and be unable to send signal, therefore losing the ability to detect for VAP.

Resolution:

A basic test cycle performed before the actual testing begins is critical in ensuring that all components are correctly connected. This test will compare expected results to actual and determine if the system is ready for use. If it is determined that the actual results from the test cycle were outside the accepted range than the test will not run and the hospital staff will be required to check connections on everything.

Voltmeter
Risk:

The risk associated with the voltmeter consists of false outputs based on the specific input. This would lead to errors when using the voltmeter readings to calculate results, which would make the device unfit for use in diagnosing VAP. All of the electrical components in the device must work together in order for the system to work, the voltmeters role in that is turning the signal output from the probe into usable data. If it is not working correctly the device provides no added benefit and would be better left out of the ventilator pathway.

Resolution:

Inaccurate readings from the voltmeter will stem from improper calibration and set up. If confirmed that the voltmeter is inserted into the system properly based on previous risk mitigation steps, we would be able to confirm that unexpected results are due to the voltmeter itself. Controlling the function of the voltmeter during testing is difficult but we are able to decrease the RPN associated with voltmeter by using control data to test the system is working as expected prior to exposing to mucus. This would consist of sending a known signal using the function generator to start the test and analyzing the results from the voltmeter. If the values are within an expected threshold, the test will continue as normal, if they are out of the range the test will not progress and recommend system checks.

Arduino Alert System

Risk:

The first of the possible risks associated with the Arduino Alert System is that the medical do not receive notification of the development of VAP in patients. This could be due to either a lost connection between the sensor and the alert system or a failure within the alert system itself. This presents a huge problem for us as in order for our goal of diagnosing VAP to be met, someone must be told to intervene. The second risk is that an alert is given but it is not responded to due to it blending in with the noise of other hospital alerts. This also presents a similar issue in which the device loses its main functionality. The third risk associated with the actual data analyzation occurring within the single board computer giving an incorrect update to the status of VAP, either false positive, or false negative.

Resolution:

In order to combat the first risk, during the initial pre-testing cycle for systems check, the device will ensure that the arduino is receiving the same results sent by the rest of the system and components, and that the alarm is working properly. If either of these processes is not working as expected, the system will not run and suggest checking of connections or maintenance. The second risk is reduced by including a unique and loud alarm system, this will allow hospital staff to differentiate it from other devices in the room. Lastly in order to prove that we accurately identifying VAP, we will build in different impedance spectrum of bacteria specific to VAP, allowing for us to monitor multiple types of possible causes. During testing we will also have to determine the appropriate changes in impedance at specific frequencies that should give suspicion to the presence of VAP. Both of the problems dealing with the algorithms the arduino is running will need to be solved during the product testing phase, following confirmation of proof of concept.

Reference Values for Device

Required Endotracheal Tube Measurements:
  Range of Endotracheal tube inner diameters: 2.50-9.5 mm
  Range of Endotracheal tube outer diameters: 3.4-13 mm
  Average Endotracheal Tube Length for Females: 210 mm
  Average Endotracheal Tube Length for Males: 230 mm
  Endotracheal tubing thickness: changes depending on inner/outer diameter sizing
  Average Endotracheal tube angle: ~85 degrees, but changes depending on tube sizing Impedance Measurements:
  2V (vs. OCP) potential across working electrode for 3 min followed by potential of 2V (vs. OCP) for 3 more minutes
  200 mVrms perturbation potential (vs. OCP)
  Range of frequencies needed: 1 Hz-100 KHz
  Impedance measurements are used using equations in appendix A2, in which the arduino will calculate impedance at individual frequencies and form spectrum at time points
  Sensitivity: Lowest tested concentration was $1.8 \times 10^6$ CFU/ml after 30 minutes guaranteed (A bacterial infection is also quantified as CFU/ml greater than $10^6$)

Other bacterial strains have been found using EIS as well, and have shown that EIS is an effective way of measuring the presence of what type of bacteria and their concentration. They have not been tested using this system so they will not be included and only *Staphylococcus* will be included.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. An apparatus for detection of ventilator associated pneumonia (VAP) in a patient, the apparatus comprising:
  an endotracheal tube;
    at least two non-selective electrode contacts located in proximity to each other within the endotracheal tube, the contacts lacking any structural feature or component that particularly recognizes a chemical or biological species;
    an electrical subsystem that is capable of generating, receiving and processing electrical signals;
    wiring for connecting each of the electrode contacts with the electrical subsystem; and tubing for insulating the wiring from any sputum material that is introduced into the endotracheal tube by the patient,
    wherein the electrical subsystem generates at least two distinct and oscillating electrical signals, the distinct electrical signals having distinct frequencies, each electrical signal being associated with an oscillating current that passes through the sputum material, enabling the electrical subsystem to calculate an impedance associated with each electrical signal, the plurality of impedances constituting a pattern of impedances; and
    wherein the pattern of impedances correlates with a presence of one or more species of bacteria, wherein the apparatus is configured to determine a relative concentrations of the species of bacteria.

2. The apparatus of claim 1, wherein the pattern of impedances correlates with a particular species of bacteria.

3. The apparatus of claim 2, wherein the species of bacteria is selected from the group consisting of *Pseudomonas* spp. (including *P. aeruginosa*), *Streptococcus* spp. (including *S. pneumoniae* and *S. aureus*), *Hemophilus* spp. (including *Hemophilus influenza*), *Escherichia coli*, *Klebsiella* spp. (including *Klebsiella pneumonia*), *Enterobacter* spp., *Proteus* spp., *Serratia* spp. (including *Serratia marcescens*), *Acinetobacter* spp., *Citrobacter* spp., *Neisseria* spp., *Stenotrophomonas maltophilia*, *Corynebacterium* spp., *Moraxella* spp. and *Enterococcus* spp.

4. The apparatus of claim 1, further comprising a computer that assists the electrical subsystem with signal processing and identification of one or more bacterial species that is/are present in the sputum material.

5. The apparatus of claim 1, wherein the electrode contacts are gold plated.

6. The apparatus of claim 1, wherein contact surfaces of the electrode contacts are carbon, platinum, or nickel.

7. The apparatus of claim 1, wherein the insulating tubing is silicone tubing.

8. The apparatus of claim 1, wherein the insulating tubing is fixed to an inside surface of the endotracheal tube with a biocompatible adhesive.

9. The apparatus of claim 1, wherein the insulating tubing is continuous with an inside surface of the endotracheal tube.

10. The apparatus of claim 1, wherein the wiring comprises a chromium/nickel/molybdenum alloy.

11. The apparatus of claim 1, wherein the endotracheal tube has an internal diameter of about 7.5 mm.

12. The apparatus of claim 1, wherein each electrode contact is separated by a gap of about 0.8 mm from another electrode contact.

13. The apparatus of claim 12, wherein sputum material fills the gap(s).

14. A method for detecting ventilator associated pneumonia (VAP) in a patient, the method comprising:

placing an endotracheal tube through the mouth and into the trachea of the patient, wherein there are at least two electrode contacts located in proximity to each other within the endotracheal tube on an inside surface of the endotracheal tube, wherein insulated conductive wiring connects the electrode contacts with an electrical subsystem that is capable of generating, receiving and processing electrical signals;

directing the electrical subsystem to sequentially provide at least two alternating current signals to the electrode contacts, thereby allowing the electrical subsystem to derive an impedance corresponding to each alternating current signal, the multiple derived impedances forming a pattern of impedances;

matching the pattern of impedances to a pattern of impedances known to be associated with a particular bacterial pathogen or a particular combination of bacterial pathogens; and further comprising using the impedance data to determine a concentration of the particular bacterial pathogen or to determine a concentration for each pathogen in the combination of bacterial pathogens.

15. The apparatus of claim 1, further comprising an infrared optical sensor fitted to exhaled breath tubing that is in communication with the endotracheal tube.

16. The apparatus of claim 1, further comprising a semiconductor gas sensor fitted to exhaled breath tubing that is in communication with the endotracheal tube.

* * * * *